United States Patent [19]
Williams et al.

[11] Patent Number: 5,913,813
[45] Date of Patent: Jun. 22, 1999

[54] DOUBLE-WALL BALLOON CATHETER FOR TREATMENT OF PROLIFERATIVE TISSUE

[75] Inventors: Jeffery A. Williams, Baltimore, Md.; Christopher H. Porter, Woodinville, Wash.; Jeffrey F. Williamson; James F. Dempsey, both of St. Louis, Mo.; Timothy J. Patrick; James B. Stubbs, both of Alpharetta, Ga.

[73] Assignee: Proxima Therapeutics, Inc., Alpharetta, Ga.

[21] Appl. No.: 08/900,021

[22] Filed: Jul. 24, 1997

[51] Int. Cl.$^6$ ....................................................... A61N 5/00
[52] U.S. Cl. ................................................................. 600/3
[58] Field of Search ............................................... 600/1–8

[56] References Cited

U.S. PATENT DOCUMENTS

| | | |
|---|---|---|
| 3,324,847 | 6/1967 | Zoumboulis . |
| 5,106,360 | 4/1992 | Ishiwara et al. . |
| 5,429,582 | 7/1995 | Williams . |
| 5,611,767 | 3/1997 | Williams . |
| 5,662,580 | 9/1997 | Bradshaw et al. ........................ 600/3 |
| 5,782,742 | 7/1998 | Crocker et al. . |
| 5,785,688 | 7/1998 | Joshi et al. . |

*Primary Examiner*—John P. Lacyk
*Attorney, Agent, or Firm*—Nikolai, Mersereau & Dietz, P.A.

[57] ABSTRACT

An instrument for use in brachytherapy comprises a concentric arrangement of inner and outer distensible, spherical chambers disposed near the proximal end of a catheter body where one of the chambers is made to contain a radioactive material with the other chamber containing a radiation absorptive material, the apparatus functioning to provide a more uniform absorbed dose profile in tissue surrounding a cavity created by the removal of a tumor. An alternative embodiment includes non-spherical inner and outer chambers whose respective walls are spaced equidistant over the entire surfaces thereof.

13 Claims, 2 Drawing Sheets

DOUBLE-WALL BALLOON CATHETER FOR TREATMENT OF PROLIFERATIVE TISSUE

BACKGROUND OF THE INVENTION

I. Field of the Invention

This invention relates generally to apparatus for use in treating proliferative tissue disorders, and more particularly to an apparatus for the treatment of such disorders in the body by the application of radioactive material and/or radiation emissions.

II. Discussion of the Prior Art

In the Williams U.S. Pat. No. 5,429,582 entitled "Tumor Treatment", there is described a method and apparatus for treating tissue surrounding a surgically excised tumor with radioactive emissions to kill any cancer cells that may be present in the margins surrounding the excised tumor. In accordance with that patent, there is provided a catheter having an inflatable balloon at a distal end thereof to define a distensible reservoir. Following surgical removal of a tumor, say in the brain or breast, the deflated balloon may be introduced into the surgically-created pocket left following removal of a tumor and then the balloon is inflated by injecting a fluid having radionuclide(s) therein into the distensible reservoir, via a lumen in the catheter.

When it is considered that the absorbed dose rate at a point exterior to the radioactive source is inversely proportional to the square of the distance between the radiation source and the target point, tissue directly adjacent the wall of the distensible reservoir may be overly "hot" to the point where healthy tissue necrosis may result. In general, the amount of radiation desired by the physician is a certain minimum amount that is delivered to a site 0–3 cms away from the wall of the excised tumor. It is desirable to keep the radiation in the space between that site and the wall of the distensible reservoir as uniform as possible to prevent overexposure to tissue at or near the reservoir wall. In treating other cancers, such as bladder cancer, where the neoplastic tissue is generally located on the bladder surface, deep penetration is unnecessary and to be avoided.

A need exists for an instrument which may be used to deliver radiation from a radioactive source to target tissue within the human body of a desired intensity and at a predetermined distance from the radiation source without over-exposure of body tissues disposed between the radiation source and the target.

SUMMARY OF THE INVENTION

We have found that it is possible to deliver a desired radiation dose at a predetermined radial distance from a source of radioactivity by providing a first spacial volume at the distal end of a catheter and a second spacial volume defined by a surrounding of the first spatial volume by a polymeric film wall where the distance from the spatial volume and the wall is maintained substantially constant over their entire surfaces. One of the inner and outer volumes is filled with either a fluid or a solid containing a radionuclide(s) while the other of the two volumes is made to contain either a low radiation absorbing material, e.g., air or even a more absorptive material, such as an x-ray contrast fluid. Where the radioactive material comprises the core, the surrounding radiation absorbing material serves to control the radial profile of the radioactive emissions from the particular one of the inner and outer volumes containing the radionuclide(s) so as to provide a more radially uniform radiation dosage in a predetermined volume surrounding the outer chamber. Where the core contains the absorbent material, the radial depth of penetration of the radiation can be tailored by controlling the core size.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which.

DESCRIPTION OF THE PREFERRED EMBODIMENT

Figure 1:
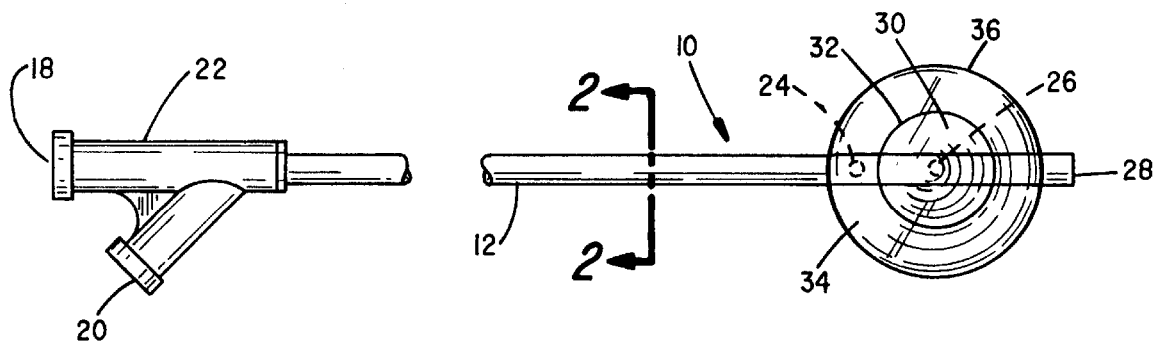
FIG. 1 is a side view of an apparatus for delivering radioactive emissions to body tissue.
Figure 2:
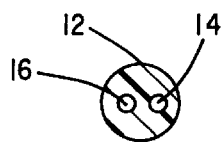
FIG. 2 is a cross-sectional view taken along the line 2—2 in FIG. 1.

Referring first to FIG. 1, there is indicated generally by numeral 10 a surgical instrument for providing radiation treatment to proliferative tissue in a living patient. It is seen to comprise a tubular body member 12 having first and second lumens 14 and 16 (FIG. 2) extending from proximal ports 18 and 20 in a molded plastic hub 22 to inflation ports 24 and 26 formed through the side wall of the tube 12 and intersecting with the lumens 14 and 16, respectively.

Affixed to the tubular body 12 proximate the distal end 28 thereof is an inner spatial volume 30 which may be defined by a generally spherical polymeric film wall 32. The interior of the chamber 30 is in fluid communication with the inflation port 26. Surrounding the spatial volume 30 is an outer chamber 34 defined by an outer polymeric film wall 36 that is appropriately spaced from the wall 32 of the inner chamber 30 when the two chambers are inflated or otherwise filled and supported. Chamber 34 encompasses the inflation port 24.

The embodiment of FIG. 1 can be particularly described as comprising two spherical chambers 30 and 34, one inside the other. In accordance with a first embodiment of the invention, the outer chamber 34, being the volume defined by the space between the inner spherical wall 32 and the outer spherical wall 36, may be filled with air or, alternatively, a radiation absorbing fluid, such as a contrast media used in angiography. The inner chamber 30 is then filled with a material containing a predetermined radionuclide, for example, I-125, I-131, Yb-169 or other source of radiation, such as radionuclides that emit photons, beta particles or other therapeutic rays.

Those skilled in the art will appreciate that instead of having the inner spatial volume 30 defined by a generally spherical polymeric film wall as at 32, the catheter body member 12 may have a solid spherical radiation emitting material in which event that solid sphere would be surrounded with the outer spherical wall 36 with the spatial volume therebetween occupied by a radioactive ray absorbent material, such as air, water or a contrast material.

Figure 5:
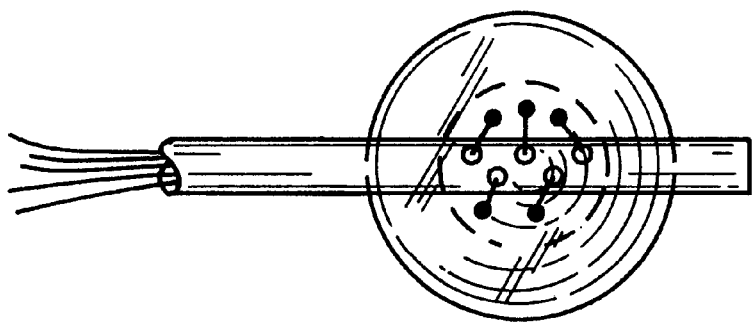
FIG. 5 depicts a further embodiment of the invention.

It is further contemplated that instead of having the inner spatial volume comprising a single solid sphere, it may instead comprise a plurality of radioactive particles strategically placed within the inner spatial volume so as to radiate in all directions with a substantially equal intensity. FIG. 5 illustrates a catheter having the inner spatial volume occupied by a plurality of radioactive beads that are mounted on the distal ends of a plurality of wires that are routed through the catheter body and exit a plurality of ports formed through the wall of the catheter body and reaching the lumen. This arrangement allows the exact positioning of the individual radiation sources to be positioned so as to generate a desired resultant profile.

Figure 3:
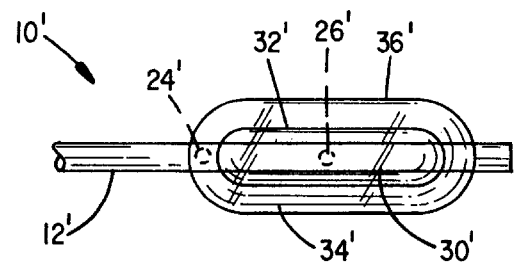
FIG. 3 is a fragmentary side view of an apparatus for administering radiation therapy in accordance with a second embodiment.

It is not essential to the invention that the chambers 30 and 34 have spherical walls, so long as the spacing between the wall of the inner chamber and the wall of the outer chamber remain generally constant, such as is illustrated in FIG. 3.

Figure 4:
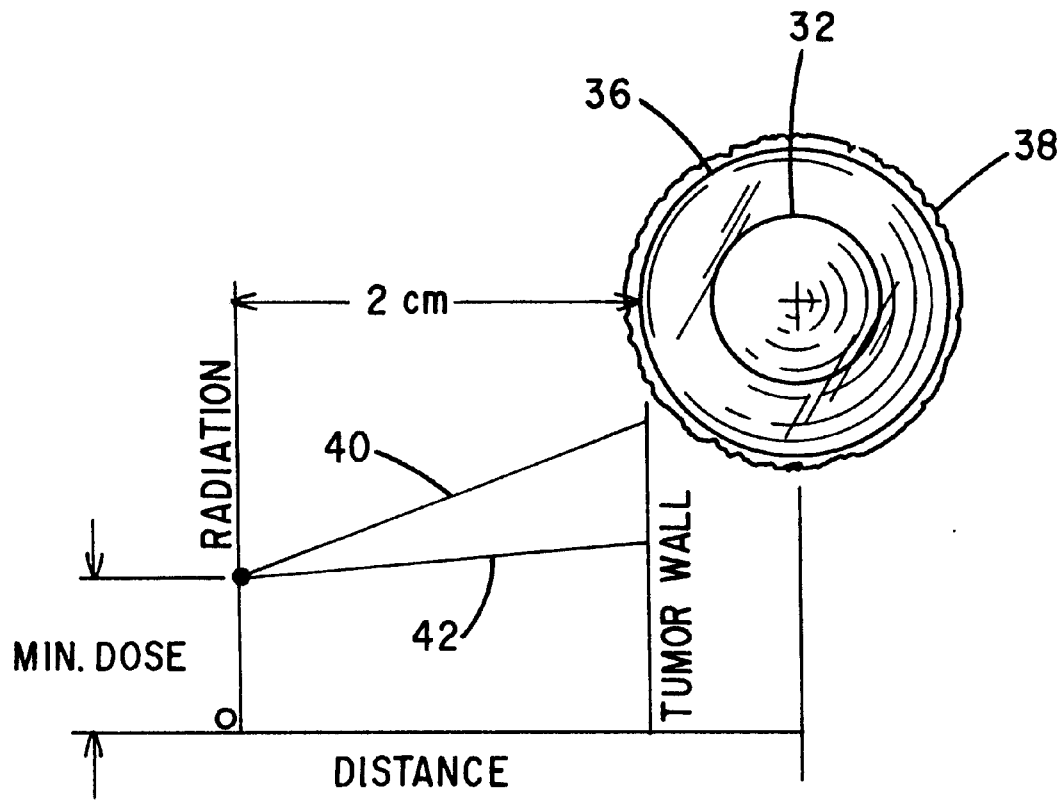
FIG. 4 is a graph helpful in understanding the operation of the apparatus of the present invention.

Referring to FIG. 4, there is shown the two concentric spherical chambers of FIG. 1 defined by inner spherical wall 32 and outer spherical wall 36 disposed within the margin 38 of a surgically excised tumor. It is desired that the radiation emitted from the core 32 be capable of delivering a certain minimum dose absorbed at a location approximately 0-3 cms from the margin 38. Curve 40 is a plot of absorbed dose vs. radial distance that would be obtained if the inner chamber defined by spherical wall 32 was not present and the entire volume of the spherical chamber defined by wall 36 were filled with the radioactive fluid. Plot 42 reflects the absorbed dose distribution as a function of radial distance when the radioactive fluid is contained within the inner chamber and is surrounded by either a gas or a more radiation absorbing material. Comparing the plots 40 and 42, by providing the concentric arrangement depicted, the absorbed dose profile in the space between the 2 cm site and the wall of the outer balloon is maintained much more uniform, thus preventing over-treatment of body tissue at or close to the outer wall 36 of the instrument. That is to say, to obtain the same end point absorbed dose at 2 cm, it would be necessary to increase the source activity relative to that used for a completely filled (to surface 36) configuration, assuming the same radionuclide is used in both configurations.

With no limitation intended, the distensible polymeric chambers may comprise a biocompatible, radiation resistant polymer, such as Silastic rubbers, polyurethanes, polyethylene, polypropylene, polyester, PVC, C-Flex. The radioactive fluid contained within the inner chamber 32 can be made from any solution of radionuclide(s), e.g., a solution of I-125 or I-131. A radioactive fluid can also be produced using a slurry of a suitable fluid containing small particles of solid radionuclides, such as Au-198, Y-90. Moreover, the radionuclide(s) can be embodied in a gel.

In the embodiments heretofore described, the material containing the radionuclide(s) is located in the inner chamber. The invention also contemplates that the outer chamber 34 may contain the material having the radionuclide therein while the inner chamber 30 contains the radiation absorptive material. This configuration is advantageous where a profile exhibiting higher intensity at a tissue surface with lesser penetration is desired. By using this approach, less volume of radioactive material is required than if the entire volume of the device were filled with radioactive material. Moreover, the outer chamber wall need not be spherical, yet a uniform profile is obtainable. Experiments have shown that a steeper radial absorbed source gradient can be obtained using a radiation attenuation fluid in the inner chamber 30 than otherwise obtains when only a single distensible chamber is used, as in the aforereferenced Williams U.S. Pat. No. 5,429,582. The invention also contemplates that the radioactive material in the inner core can be replaced by a core containing solid radionuclide-containing particles. For example, radioactive micro spheres of the type available from the 3M Company of St. Paul, Minn., may be used in place of the fluid. This radioactive source can either be preloaded into the catheter at the time of manufacture or loaded into the device after it has been implanted into the space formerly occupied by the excised tumor. Such a solid radioactive core configuration offers the advantage in that it allows a wider range of radionuclides than if one is limited to liquids. Solid radionuclides that could be used with the delivery device of the present invention are currently generally available as brachytherapy radiation sources.

In either the concentric spherical embodiment of FIG. 1 or the non-spherical configuration of FIG. 3, the spacing between the inner and outer chambers needs to be held somewhat constant to avoid "hot spots". This result can be achieved by careful placement of precision blown polymer parisons or by using compressible foams or mechanical spacers in the form of webs joining the inner wall 32 to the outer wall 36.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. Apparatus for delivering radioactive emissions to a body location with a uniform radiation profile, comprising:

(a) a catheter body member having a proximal end and distal end;

(b) an inner spatial volume disposed proximate the distal end of the catheter body member;

(c) an outer, closed, inflatable, chamber defined by a radiation transparent wall affixed to the body member proximate the distal end thereof in surrounding relation to the inner spatial volume with a predetermined constant spacing between said inner spatial volume and the radiation transparent wall;

(d) a material containing a radionuclide(s) disposed in one of the inner spatial volume and outer chamber; and (e) means disposed in the other of the inner spatial volume and outer chamber for rendering uniform the radial absorbed dose profile of the emissions from the one of the inner spatial volume and outer chamber containing the radionuclides.

2. The apparatus as in claim 1 wherein said inner spatial volume is an inner closed, chamber defined by a further radiation transparent wall.

3. The apparatus of claim 1 wherein the means for rendering uniform the absorbed dose profile is a radiation attenuating material.

4. The apparatus of claim 3 wherein the radiation attenuating material is selected from a group consisting of barium sulphate, water, and X-ray contrast media.

5. The apparatus as in claim 2 wherein the radionuclide is in a fluid form.

6. The apparatus as in claim 5 wherein the fluid comprises an isotope of iodine.

7. The apparatus as in claim 1 wherein the radionuclide is a slurry of a fluid containing particles of a solid isotope.

8. The apparatus as in claim 2 wherein the inner chamber contains the radioactive material.

9. The apparatus as in claim 1 wherein the outer chamber contains the radioactive material.

10. The apparatus as in claim 8 wherein the radioactive material is a fluid.

11. The apparatus as in claim 8 wherein the radioactive material is a solid.

12. The apparatus as in claim 1 wherein the material containing a radionuclide comprises a plurality of radioactive solid particles placed at predetermined locations within the inner spatial volume to provide a desired composite radiation profile.

13. The apparatus as in claim 2 wherein the inner and outer chambers are spherical in shape and are concentric.

* * * * *